US006190406B1

(12) United States Patent
Duerig et al.

(10) Patent No.: US 6,190,406 B1
(45) Date of Patent: Feb. 20, 2001

(54) INTRAVASCULAR STENT HAVING TAPERED STRUTS

(75) Inventors: Thomas Duerig, Freemont, CA (US); Janet Burpee, Fair Haven, NJ (US); Mark Mathis, Fremont, CA (US)

(73) Assignee: Nitinal Development Corporation, Fremont, CA (US)

( * ) Notice: Under 35 U.S.C. 154(b), the term of this patent shall be extended for 0 days.

(21) Appl. No.: 09/241,985

(22) Filed: Feb. 2, 1999

Related U.S. Application Data

(63) Continuation-in-part of application No. 09/005,401, filed on Jan. 9, 1998, now Pat. No. 6,129,755, and a continuation-in-part of application No. 09/005,402, filed on Jan. 9, 1998.

(51) Int. Cl.⁷ .................................................... A61F 2/06
(52) U.S. Cl. ............................................. 623/1.2; 623/1.15
(58) Field of Search .................................. 623/1.1, 1.15, 623/1.16, 1.18, 1.19, 1.2, 1.35

(56) References Cited

U.S. PATENT DOCUMENTS

| 4,925,445 | * | 5/1990 | Sakamoto et al. | 604/95 |
| 5,104,404 | * | 4/1992 | Wolff | 623/1 |
| 5,776,161 | * | 7/1998 | Globerman | 606/194 |
| 5,830,179 | * | 11/1998 | Mikus et al. | 604/49 |
| 5,876,449 | * | 3/1999 | Starck et al. | 623/12 |
| 6,042,606 | * | 3/2000 | Frantzen | 623/1 |

FOREIGN PATENT DOCUMENTS

96/26689  *  9/1996  (WO) .

* cited by examiner

Primary Examiner—Michael J. Milano
Assistant Examiner—Hieu Phan

(57) ABSTRACT

In accordance with the present invention, there is provided a stent, preferably a self-expanding Nitinol stent, for insertion into a vessel of a patient. The stent is made from a tubular member a thickness, front and back open ends, and a longitudinal axis extending therebetween. The member has a first smaller diameter for insertion into a vessel, and a second larger diameter for deployment into a vessel. The tubular member has a plurality of adjacent hoops extending between its front and back ends. The hoops are formed of a plurality of longitudinal struts, each having opposing ends and a center therebetween. The ends of the struts are shaped to form a plurality of loops which connect adjacent struts at the ends of the struts. The member further includes a plurality of bridges connecting adjacent hoops to one another. Each of the struts has a width which is greater at its ends than at its center. Preferably, the width continuously tapers from a greater width at the ends to a smaller width at the centers.

16 Claims, 5 Drawing Sheets

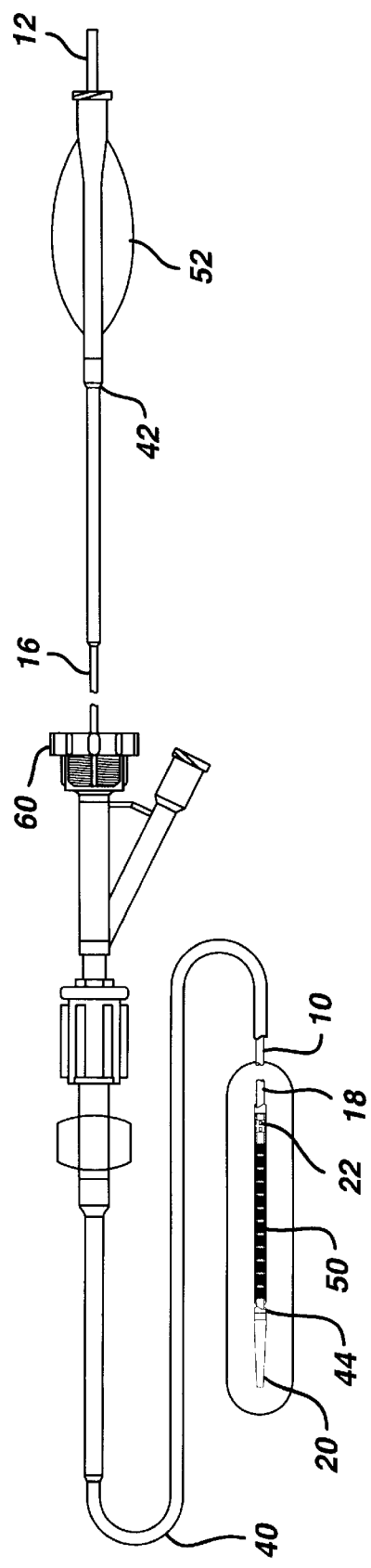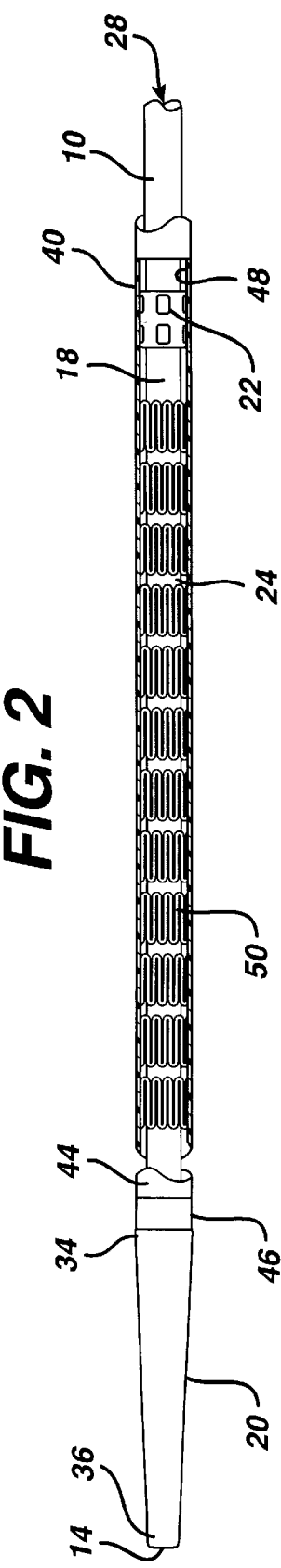

INTRAVASCULAR STENT HAVING TAPERED STRUTS

This is a continuation-in-part of application Ser. No. 09/005,401, filed Jan. 9, 1998, now U.S. Pat. No. 6,129,775 and a continuation-in-part application Ser. No. 09/005,402, filed Jan. 9, 1998.

FIELD OF THE INVENTION

The present invention relates to expandable intraluminal grafts ("stents") for use within a body passageway or duct which are particularly useful for repairing blood vessels narrowed or occluded by disease. The present invention relates even further to such stents which are self-expanding and made from a superelastic material such as Nitinol.

BACKGROUND OF THE INVENTION

Percutaneous transluminal coronary angioplasty (PTCA) is a therapeutic medical procedure used to increase blood flow through the coronary artery and can often be used as an alternative to coronary by-pass surgery. In this procedure, the angioplasty balloon is inflated within the stenosed vessel, or body passageway, in order to shear and disrupt the wall components of the vessel to obtain an enlarged lumen. With respect to arterial stenosed lesions, the relatively incompressible plaque remains unaltered, while the more elastic medial and adventitial layers of the body passageway stretch around the plaque. This process produces dissection, or a splitting and tearing, of the body passageway wall layers, wherein the intima, or internal surface of the artery or body passageway, suffers fissuring. This dissection forms a "flap" of underlying tissue which may reduce the blood flow through the lumen, or block the lumen. Typically, the distending intraluminal pressure within the body passageway can hold the disrupted layer, or flap, in place. If the intimal flap created by the balloon dilation procedure is not maintained in place against the expanded intima, the intimal flap can fold down into the lumen and close off the lumen, or may even become detached and enter the body passageway. When the intimal flap closes off the body passageway, immediate surgery is necessary to correct the problem.

Recently, transluminal prostheses have been widely used in the medical arts for implantation in blood vessels, biliary ducts, or other similar organs of the living body. These prostheses are commonly known as stents and are used to maintain, open, or dilate tubular structures. An example of a commonly used stent is given in U.S. Pat. No. 4,733,665 filed by Palmaz on Nov. 7, 1985, which is hereby incorporated herein by reference. Such stents are often referred to as balloon expandable stents. Typically the stent is made from a solid tube of stainless steel. Thereafter, a series of cuts are made in the wall of the stent. The stent has a first smaller diameter which permits the stent to be delivered through the human vasculature by being crimped onto a balloon catheter. The stent also has a second, expanded diameter, upon the application, by the balloon catheter, from the interior of the tubular shaped member of a radially, outwardly directed force.

However, such stents are often impractical for use in some vessels such as the carotid artery. The carotid artery is easily accessible from the exterior of the human body, and is often visible by looking at ones neck. A patient having a balloon expandable stent made from stainless steel or the like, placed in their carotid artery might be susceptible to sever injury through day to day activity. A sufficient force placed on the patients neck, such as by falling, could cause the stent to collapse, resulting in injury to the patient. In order to prevent this, self expanding stents have been proposed for use in such vessels. Self expanding stents act like springs and will recover to their expanded or implanted configuration after being crushed.

One type of self-expanding stent is disclosed in U.S. Pat. No. 4,665,771, which stent has a radially and axially flexible, elastic tubular body with a predetermined diameter that is variable under axial movement of ends of the body relative to each other and which is composed of a plurality of individually rigid but flexible and elastic thread elements defining a radially self-expanding helix. This type of stent is known in the art as a "braided stent" and is so designated herein. Placement of such stents in a body vessel can be achieved by a device which comprises an outer catheter for holding the stent at its distal end, and an inner piston which pushes the stent forward once it is in position.

However, braided stents have many disadvantages. They typically do not have the necessary radial strength to effectively hold open a diseased vessel. In addition, the plurality of wires or fibers used to make such stents could become dangerous if separated from the body of the stent, where it could pierce through the vessel. Therefore, there has been a desire to have a self-expanding stent, which is cut from a tube of metal, which is the common manufacturing method for many commercially available balloon expandable stents. In order to manufacture a self-expanding stent cut from a tube, the alloy used would preferably exhibits superelastic or psuedoelastic characteristics at body temperature, so that it is crush recoverable.

The prior art makes reference to the use of alloys such as Nitinol (Ni—Ti alloy) which have shape memory and/or superelastic characteristics in medical devices which are designed to be inserted into a patient's body. The shape memory characteristics allow the devices to be deformed to facilitate their insertion into a body lumen or cavity and then be heated within the body so that the device returns to its original shape. Superelastic characteristics on the other hand generally allow the metal to be deformed and restrained in the deformed condition to facilitate the insertion of the medical device containing the metal into a patient's body, with such deformation causing the phase transformation. Once within the body lumen the restraint on the superelastic member can be removed, thereby reducing the stress therein so that the superelastic member can return to its original un-deformed shape by the transformation back to the original phase.

Alloys having shape memory/superelastic characteristics generally have at least two phases. These phases are a martensite phase, which has a relatively low tensile strength and which is stable at relatively low temperatures, and an austenite phase, which has a relatively high tensile strength and which is stable at temperatures higher than the martensite phase.

Shape memory characteristics are imparted to the alloy by heating the metal at a temperature above which the transformation from the martensite phase to the austenite phase is complete, i.e. a temperature above which the austenite phase is stable (the Af temperature). The shape of the metal during this heat treatment is the shape "remembered". The heat treated metal is cooled to a temperature at which the martensite phase is stable, causing the austenite phase to transform to the martensite phase. The metal in the martensite phase is then plastically deformed, e.g. to facilitate the entry thereof into a patient's body. Subsequent heating of the deformed martensite phase to a temperature above the martensite to austenite transformation temperature causes the deformed martensite phase to transform to the austenite phase and during this phase transformation the metal reverts back to its original shape if unrestrained. If restrained, the metal will remain martensitic until the restraint is removed.

Methods of using the shape memory characteristics of these alloys in medical devices intended to be placed within a patient's body present operational difficulties. For example, with shape memory alloys having a stable martensite temperature below body temperature, it is frequently difficult to maintain the temperature of the medical device containing such an alloy sufficiently below body temperature to prevent the transformation of the martensite phase to the austenite phase when the device was being inserted into a patient's body. With intravascular devices formed of shape memory alloys having martensite-to-austenite transformation temperatures well above body temperature, the devices can be introduced into a patient's body with little or no problem, but they must be heated to the martensite-to-austenite transformation temperature which is frequently high enough to cause tissue damage and very high levels of pain.

When stress is applied to a specimen of a metal such as Nitinol exhibiting superelastic characteristics at a temperature above which the austenite is stable (i.e. the temperature at which the transformation of martensite phase to the austenite phase is complete), the specimen deforms elastically until it reaches a particular stress level where the alloy then undergoes a stress-induced phase transformation from the austenite phase to the martensite phase. As the phase transformation proceeds, the alloy undergoes significant increases in strain but with little or no corresponding increases in stress. The strain increases while the stress remains essentially constant until the transformation of the austenite phase to the martensite phase is complete. Thereafter, further increase in stress are necessary to cause further deformation. The martensitic metal first deforms elastically upon the application of additional stress and then plastically with permanent residual deformation.

If the load on the specimen is removed before any permanent deformation has occurred, the martensitic specimen will elastically recover and transform back to the austenite phase. The reduction in stress first causes a decrease in strain. As stress reduction reaches the level at which the martensite phase transforms back into the austenite phase, the stress level in the specimen will remain essentially constant (but substantially less than the constant stress level at which the austenite transforms to the martensite) until the transformation back to the austenite phase is complete, i.e. there is significant recovery in strain with only negligible corresponding stress reduction. After the transformation back to austenite is complete, further stress reduction results in elastic strain reduction. This ability to incur significant strain at relatively constant stress upon the application of a load and to recover from the deformation upon the removal of the load is commonly referred to as superelasticity or pseudoelasticity. It is this property of the material which makes it useful in manufacturing tube cut self-expanding stents. The prior art makes reference to the use of metal alloys having superelastic characteristics in medical devices which are intended to be inserted or otherwise used within a patient's body. See for example, U.S. Pat. No. 4,665,905 (Jervis) and U.S. Pat. No. 4,925,445 (Sakamoto et al.).

Prior art stents designs consist of struts that bend as the stent expands and contracts. Bending forces on struts, or beams, produce the greatest moment at the anchoring point, or loops, and become smaller, in a linear fashion, further away from the anchored ends. In the case of a stent, the result is that the greatest force, and thus deformation, is found at or near the loop, and the smallest deformations are observed at the center of the struts. This causes greater fatigue at the loops of the stent. In addition, because the highest amount of deformation occurs at the loops, the amount of force one can reasonably apply to the loops during its operation should be limited. This has the result of limiting the its minimum crimped diameter, for insertion into the body, and its maximum expanded diameter for deployment within the body.

The above problems are true for all materials, but is particularly problematic for self-expanding stents, and even more particularly for self-expanding superelastic Nitinol stents. Nitinol is capable of elastically recovering from deformations as high as about 9%. Superelastic devices, therefore, must be designed so that the areas of maximum deformation remain below this 9% limit. In the case of a stent, this means that the performance is limited by the deformations at the loops. The center sections of the struts are inactive, and not contributing to the overall superelastic process. Ideally, one would want uniform deformation along the entire strut, thus increasing the macroscopic superelastic behavior and reducing the maximum deformation strains. A stent with more uniform strain along the strut length would have the advantages of an extended fatigue lifetime, a greater expansion ratio, a higher ductility, and a flatter stress-strain plateau.

The present invention provides for a self-expanding tube cut stent which overcomes many of the disadvantages associated with the prior art stents.

SUMMARY OF THE INVENTION

In accordance with the present invention, there is provided a stent, preferably a self-expanding Nitinol stent, for insertion into a vessel of a patient. The stent is made from a tubular member having a thickness, front and back open ends, and a longitudinal axis extending therebetween. The member has a first smaller diameter for insertion into a vessel, and a second larger diameter for deployment into a vessel. The tubular member has a plurality of adjacent hoops extending between its front and back ends. The hoops are formed from a plurality of longitudinal struts, each having opposing ends and a center therebetween. The ends of the struts are shaped to form a plurality of loops which connect adjacent struts at the ends of the struts. The member further includes a plurality of bridges connecting adjacent hoops to one another. Each of the struts has a width which is greater at its ends than at its center. Preferably, the width continuously tapers from a greater width at the ends to a smaller width at the centers.

BRIEF DESCRIPTION OF DRAWINGS

The foregoing and other aspects of the present invention will best be appreciated with reference to the detailed description of the invention in conjunction with the accompanying drawings, wherein:

FIG. 1 is a simplified partial cross-sectional view of a stent delivery apparatus having a stent loaded therein, which can be used with a stent made in accordance with the present invention.

FIG. 2 is a view similar to that of FIG. 1 but showing an enlarged view of the distal end of the apparatus.

DETAILED DESCRIPTION OF THE INVENTION

Figure 3:
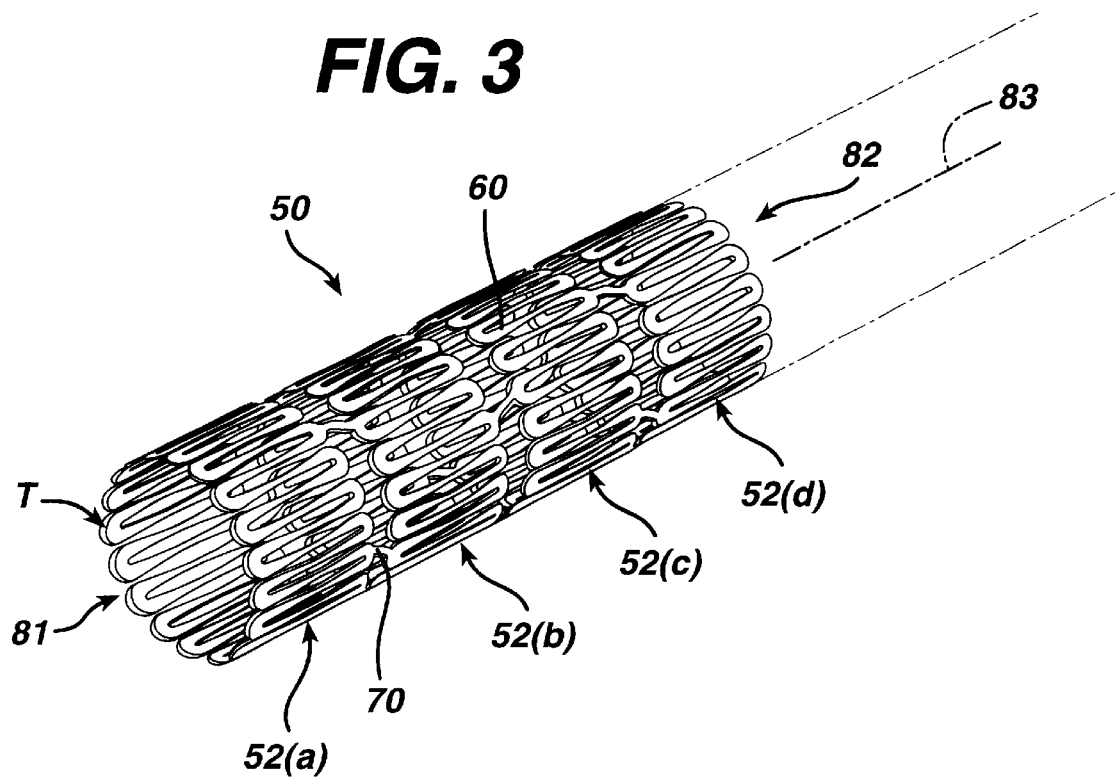
FIG. 3 is a perspective view of a stent made in accordance with the present invention, showing the stent in its compressed state.
Figure 4:
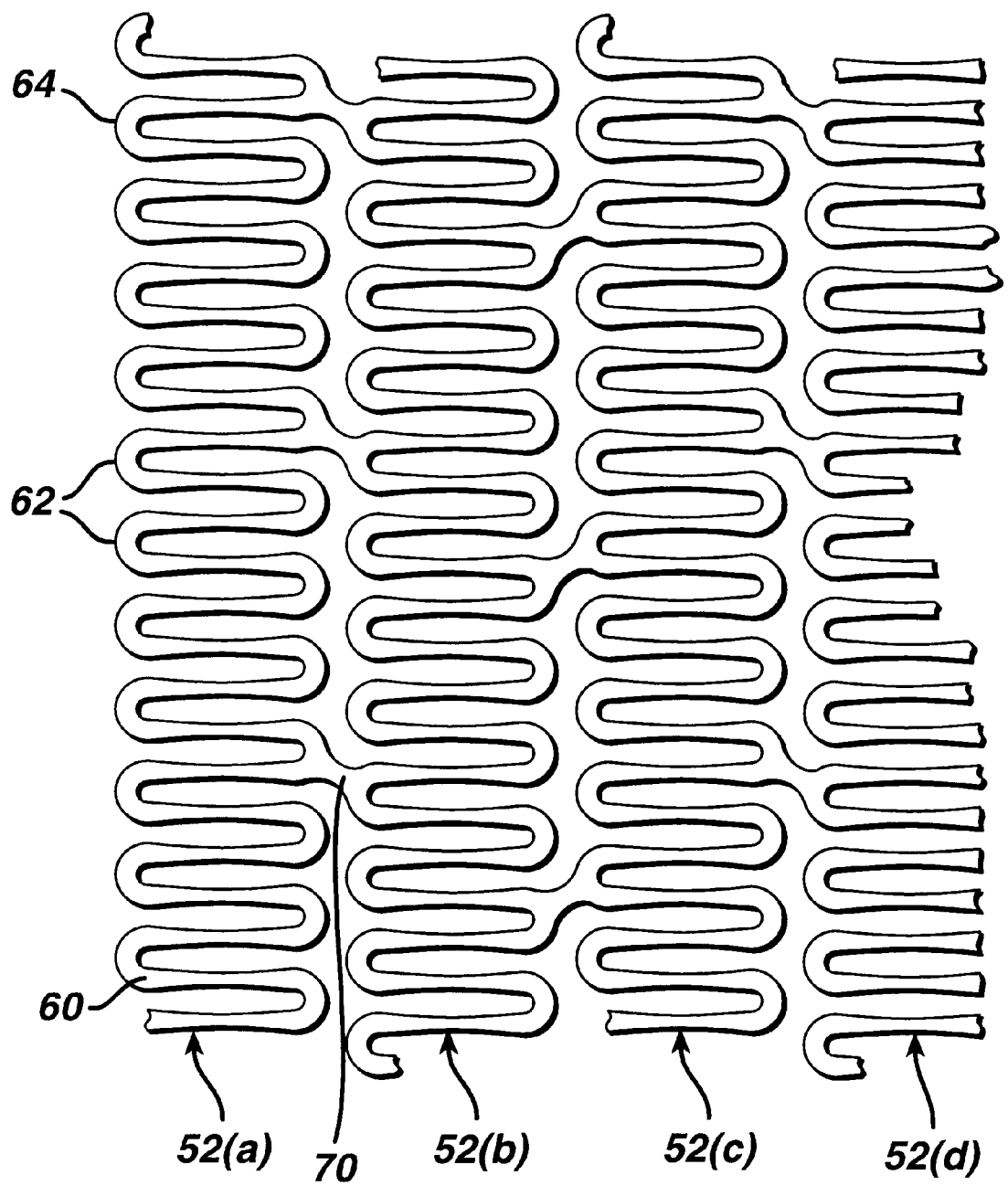
FIG. 4 is a sectional, flat view of the stent shown in FIG. 1.

Referring now to the figures wherein like numerals indicate the same element throughout the views, there is shown in FIGS. 3 and 4, a stent 50 made in accordance with the present invention. FIGS. 3 and 4 show stent 50 in its un-expanded or compressed state. Stent 50 is preferably made from a superelastic alloy such as Nitinol. Most preferably, stent 50 is made from an alloy comprising from about 50.5% (as used herein these percentages refer to atomic percentages) Ni to about 60% Ni, and most preferably about 55% Ni, with the remainder of the alloy Ti. Preferably, the stent is such that it is superelastic at body temperature, and preferably has an Af in the range from about 24° C. to about 37° C. The superelastic design of the stent makes it crush recoverable which, as discussed above, can be used as a stent or frame for any number of vascular devices for different applications.

Figure 4A:
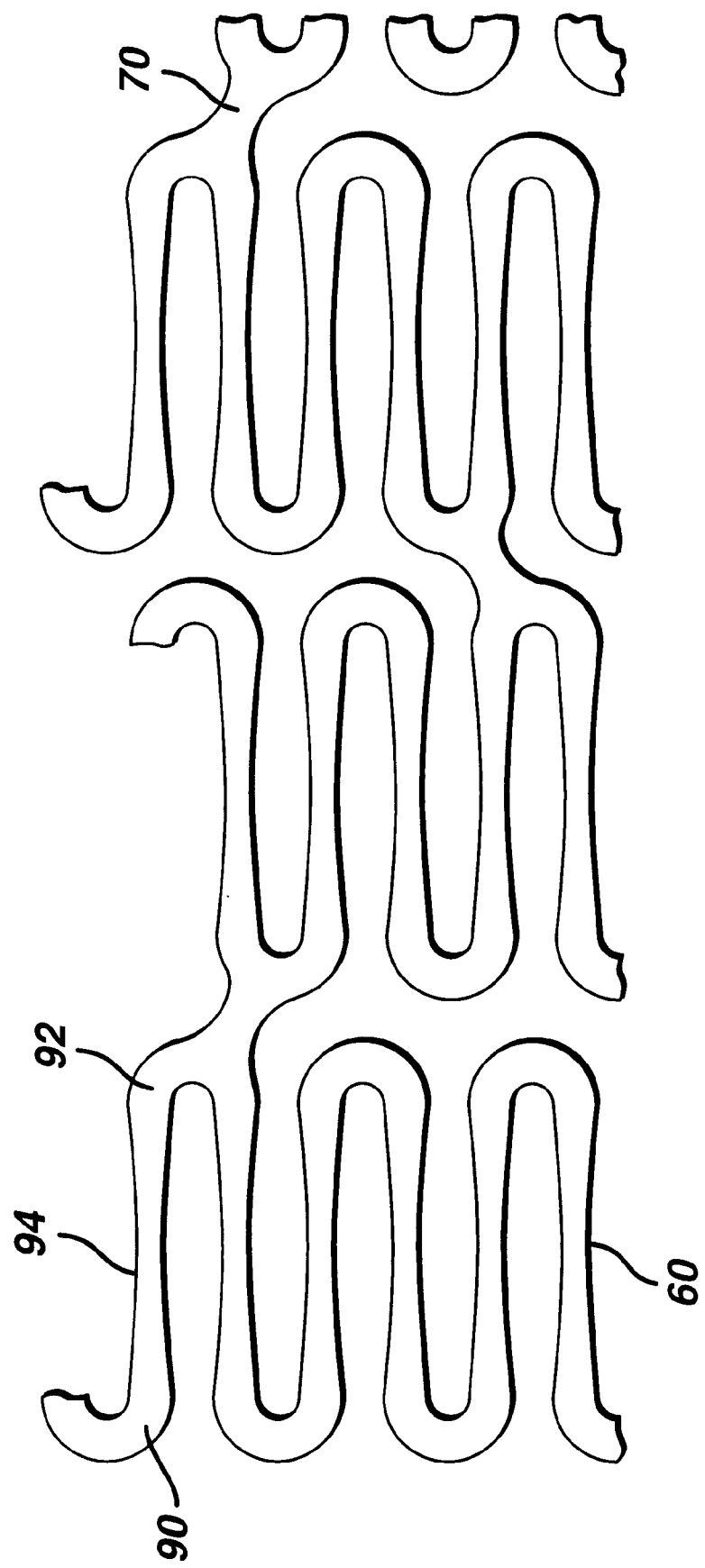
FIG. 4A is an enlarged view of section of the stent shown in FIG. 4.

Stent 50 is a tubular member having front and back open ends 81 and 82 and a longitudinal axis 83 extending therebetween. The tubular member has a first smaller diameter, FIGS. 3 and 4, for insertion into a patient and navigation through the vessels, and a second larger diameter, FIGS. 5 and 6, for deployment into the target area of a vessel. The tubular member is made from a plurality of adjacent hoops 52, FIG. 3 showing hoops 52(a)–52(d), extending between the front and back ends 81 and 82. The hoops 52 include a plurality of longitudinal struts 60. As seen from FIG. 4A, each strut 60 has two opposing ends 90 and 92 and a center 94 therebetween. The ends 92 and 94 of the struts 60 are curved or bent so as to form a plurality of loops 62, which connect adjacent struts. The struts are so connected at their opposite ends so as to form an S or Z shape pattern. The loops 62 are preferably curved substantially semi-circular and symmetrical sections.

Stent 50 further includes a plurality of bridges 70 which connect adjacent hoops 52 which can best be described by referring to FIG. 4. Each bridge has two ends, wherein one end is attached to one strut and/or loop, and another end attached to a strut and/or loop on an adjacent hoop. While the figures show the bridges connecting the loop of one bridge to the nearest loop on the adjacent hoop, this does not need to be so. The bridge could be longer and extend the length of many struts between its connection point on adjacent hoops. The bridges are curved, and are attached to loops at points off center of the radius of curvature of the loops.

The above described geometry helps to better distribute strain throughout the stent, prevents metal to metal contact when the stent is bent, and minimizes the opening size between the features, struts loops and bridges. The number of and nature of the design of the struts, loops and bridges are important factors when determining the working properties and fatigue life properties of the stent. It was previously thought that in order to improve the rigidity of the stent, that struts should be large, and therefore there should be fewer struts per hoop. However, it has now been discovered that stents having smaller struts and more struts per hoop actually improve the construction of the stent and provide greater rigidity. Preferably, each hoop has between 24 to 36 or more struts. It has been determined that a stent having a ratio of number of struts per hoop to strut length L (in inches) which is greater than 400 has increased rigidity over prior art stents which typically had a ratio of under 200. The length of a strut is measured in its compressed state parallel to the longitudinal axis 83 of the stent.

The present invention can best be understood by referring back to FIG. 4. As seen from that figure, each strut has a width W, measured in a substantially axial direction, which is greater at its ends 90 and 92, and points adjacent thereto, than in its center 94. Preferably, the width W tapers substantially continuously from the ends 90 and 92 to the center 94. The effect of this tapering will be to cause a greater resistance to deformation at the loops (where the bending moments are high), and to make the overall strain deformation more uniform. The ideal reduction in width is a complex function, driven by efforts to keep the bending radius constant. Bending of rectangular beam is controlled by the formula:

$$1/R = 12FL/(ETW^3)$$

where R is the radius of curvature of the loops (to remain constant), F is the applied force, L the distance from the endpoint, E is Young's modulus, T the thickness of the strut (shown in FIG. 3) and W the strut width. Thus as a guideline, the strut width W should vary as the cube root of the distance from the end, 90 or 92. That is, at any point along the center 94 of a strut 30 the width should be proportional to the cube root of the distance from the end that point is closest to, 90 or 92. However, any taper, even a simple linear tapered reduction in width would still represent a significant improvement over a constant width strut.

Because the struts are wider at their ends, the overall stent can handle greater compressive and expanding forces. Therefore, stents having smaller delivery diameters and greater expanded diameters can be made. In addition, the stent can handle greater fatigue stresses, which could result in a longer lasting and stronger stent.

Figure 5:
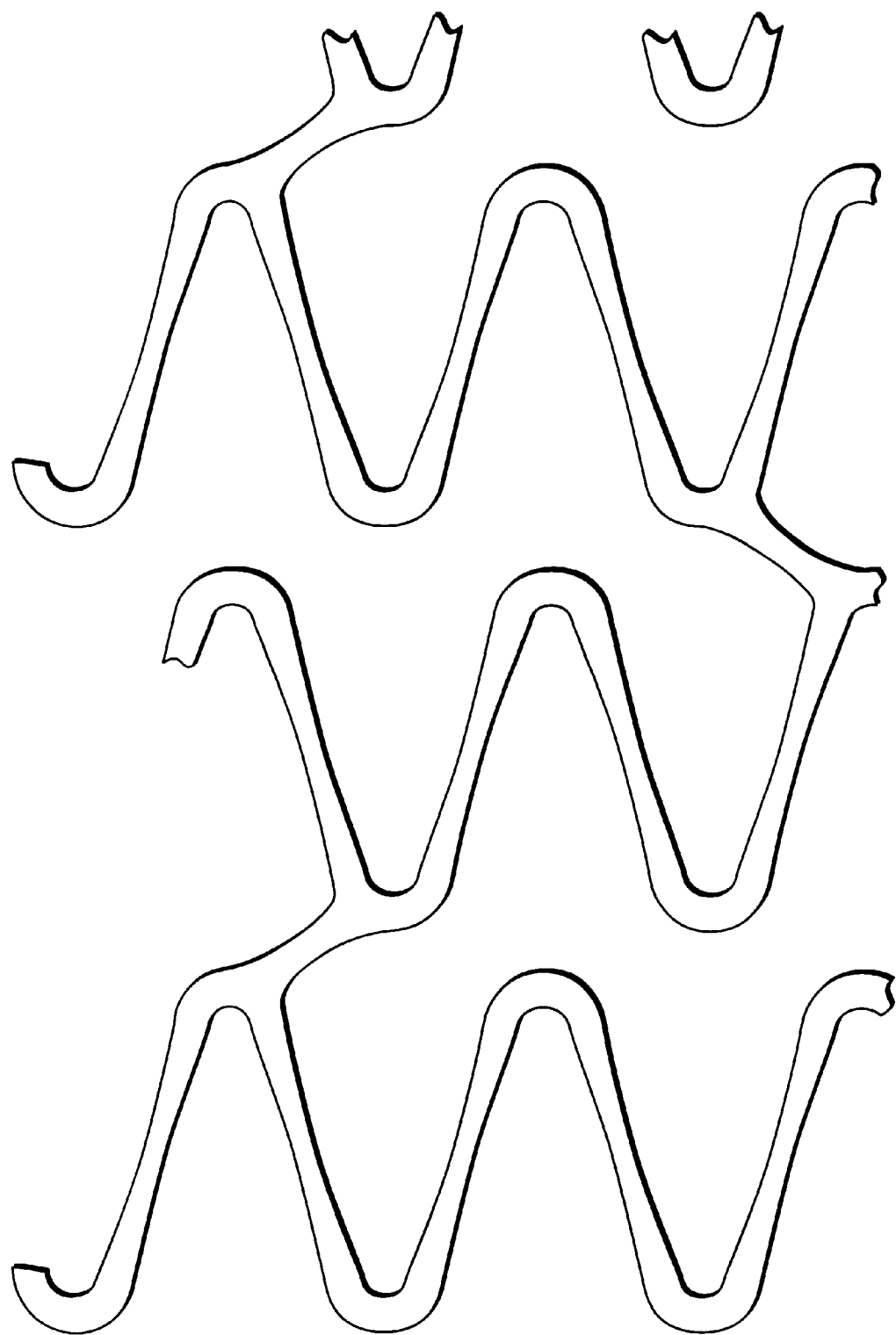
FIG. 5 is a perspective view of the stent shown in FIG. 1 but showing it in its expanded state.

As seen from FIG. 5, the geometry of the stent changes quite significantly as a stent is deployed from its un-expanded state to its expanded state. As a stent undergoes diametric change, the strut angle and strain levels in the loops and bridges are effected. Preferably, all of the stent features will strain in a predictable manor so that the stent is reliable and uniform in strength. In addition, it is preferable to minimize the maximum strain experienced by struts loops and bridges, since Nitinol properties are more generally limited by strain rather than by stress as most materials are. As will be discussed in greater detail below, the stent sits in the delivery system in its un-expanded state as shown in FIG. 3. As the stent is deployed, it is allowed to expand towards it's expanded state, as shown in FIG. 5, which preferably has a diameter which is the same or larger than the diameter of the target vessel. Nitinol stents made from wire (as opposed to being cut from a tube) deploy in much the same manor and are dependent upon the same design constraints as laser cut stents. Stainless steel stents deploy similarly in terms of geometric changes as they are assisted with forces from balloons or other devices.

In trying to minimize the maximum strain experienced by the features (struts, loops and bridges), the present invention utilizes structural geometry's which distribute strain to areas of the stent which are less susceptible to failure than others. For example, one of the most vulnerable areas of the stent is the inside radius of the connecting loops. The connecting loops undergo the most deformation of all the stent features.

The inside radius of the loop would normally be the area with the highest level of strain on the stent. This area is also critical in that it is usually the smallest radius on the stent. Stress concentrations are generally controlled or minimized by maintaining the largest radii possible, and by tapering the strut widths as disclosed above. Similarly, we want to minimize local strain concentrations on the bridge and bridge connection points. One way to accomplish this is to utilize the largest possible radii while maintaining feature widths which are consistent with applied forces. Another consideration is to minimize the maximum open area of the stent. Efficient utilization of the original tube from which the stent is cut increases stent strength and it's ability to trap embolic material.

As mentioned above bridge geometry changes as a stent is deployed from its compressed state to its expanded state and vise-versa. As a stent undergoes diametric change, strut angle and loop strain is effected. Since the bridges are connected to either the loops, struts or both, they are effected. Twisting of one end of the stent with respect to the other, while loaded in the stent delivery system, should be avoided. Local torque delivered to the bridge ends displaces the bridge geometry. If the bridge design is duplicated around the stent perimeter, this displacement causes rotational shifting of the two loops being connected by the bridges. If the bridge design is duplicated throughout the stent, as in the present invention, this shift will occur down the length of the stent. This is a cumulative effect as one considers rotation of one end with respect to the other upon deployment. A stent delivery system, such as the one described below, will deploy the distal end first, then allow the proximal end to expand. It would be undesirable to allow the distal end to anchor into the vessel wall while holding the stent fixed in rotation, then release the proximal end. This could cause the stent to twist or whip in rotation to equilibrium after it is at least partially deployed within the vessel. Such whipping action could cause damage to the vessel.

However, one embodiment of the present invention, as shown in the figures, reduces the chance of such events from happening when deploying the stent. By mirroring the bridge geometry longitudinally down the stent, the rotational shift of the Z-sections can be made to alternate and will minimize large rotational changes between any two points on a given stent during deployment or constraint. That is the bridges connecting loop 52(*b*) to loop 52(*c*) are angled upwardly from left to right, while the bridges connecting loop 52(*c*) to loop 52(*d*) are angled downwardly from left to right. This alternating pattern is repeated down the length of the stent. This alternating pattern of bridge slopes improves the torsional characteristics of the stent so as to minimize any twisting or rotation of the stent with respect to any two hoops. This alternating bridge slope is particularly beneficial if the stent starts to twist in vivo. As the stent twists, the diameter of the stent will change. Alternating bridge slopes tend to minimize this effect. The diameter of a stent having bridges which are all sloped in the same direction will tend grow if twisted in one direction and shrink if twisted in the other direction. With alternating bridge slopes this effect is minimized and localized.

The feature is particularly advantageous for stents having large expansion ratios, which in turn requires them to have extreme bending requirements where large elastic strains are required. Nitinol can withstand extremely large amounts of elastic strain deformation, so the above features are well suited to stents made from this alloy. This feature allows for maximum utilization of Ni—Ti or other material capabilities to enhance radial strength, improve stent strength uniformity, improves fatigue life by minimizing local strain levels, allows for smaller open areas which enhance entrapment of embolic material, and improves stent apposition in irregular vessel wall shapes and curves.

Preferably, stents are laser cut from small diameter tubing. For prior art stents, this manufacturing process lead to designs with geometric features, such as struts, loops and bridges, having axial widths which are larger than the tube wall thickness T (shown in FIG. 3). When the stent is compressed, most of the bending occurs in the plane that is created if one were to cut longitudinally down the stent and flatten it out. However, for the individual bridges, loops and struts, which have widths greater than their thickness, they have a greater resistance to this in-plane bending than they do to out of plane bending. Because of this, the bridges and struts tend to twist, so that the stent as a whole can bend more easily. This twisting is a buckling condition which is unpredictable and can cause potentially high strain.

However, this problem has been solved in a preferred embodiment of the present invention, shown in the figures. For the present invention, it is preferred that the maximum widths of the struts, hoops and bridges are equal to or less than the wall thickness of the tube. Therefore, substantially all bending and, therefore, all strains are "out of plane." This minimizes twisting of the stent which minimizes or eliminates buckling and unpredictable strain conditions. The feature is particularly advantageous for stents having large expansion ratios, which in turn requires them to have extreme bending requirements where large elastic strains are required. Nitinol can withstand extremely large amounts of elastic strain deformation, so the above features are well suited to stents made from this alloy. This feature allows for maximum utilization of Ni—Ti or other material capabilities to enhance radial strength, improve stent strength uniformity, improves fatigue life by minimizing local strain levels, allows for smaller open areas which enhance entrapment of embolic material, and improves stent apposition in irregular vessel wall shapes and curves.

While the current invention can be either a self expanding or balloon expandable stent, and can be made from any number of materials known in the art, including stainless steel, as mentioned above, it is preferred that the stent of the present invention be made from a superelastic alloy and most preferably made of an alloy material having greater than 50.5 atomic % Nickel and the balance titanium. Greater than 50.5 atomic % Nickel allows for an alloy in which the temperature at which the martensite phase transforms completely to the austenite phase (the Af temperature) is below human body temperature and preferably is about 24° C. to about 37° C. so that austenite is the only stable phase at body temperature.

In manufacturing the Nitinol stent, the material is first in the form of a tube. Nitinol tubing is commercially available from a number of suppliers including Nitinol Devices and Components, Fremont Calif. The tubular member is then loaded into a machine which will cut the predetermined pattern of the stent, which was discussed above and is shown in the figures, into the tube. Machines for cutting patterns in tubular devices to make stents or the like are well known to those of ordinary skill in the art and are commercially available. Such machines typically hold the metal tube between the open ends while a cutting laser, preferably under microprocessor control, cuts the pattern. The pattern dimensions and styles, laser positioning requirements, and other information are programmed into a microprocessor which controls all aspects of the process. After the stent pattern is cut, the stent is treated and polished using any number of methods well known to those skilled in the art. Lastly, the stent is then cooled until it is completely martensitic, crimped down to its un-expanded diameter and then loaded into the sheath of the delivery apparatus.

It is believed that many of the advantages of the present invention can be better understood through a brief description of a delivery apparatus for the stent, as shown in FIGS. 1 and 2. FIGS. 1 and 2 show a self-expanding stent delivery apparatus 1 for a stent made in accordance with the present invention. Apparatus 1 comprises inner and outer coaxial tubes. The inner tube is called the shaft 10 and the outer tube is called the sheath 40. Shaft 10 has proximal and distal ends 12 and 14 respectively. The distal end 14 of the shaft terminates at a luer lock hub 5. Preferably, shaft 10 has a proximal portion 16 which is made from a relatively stiff material such as stainless steel, Nitinol, or any other suitable material, and an distal portion 18 which is made from a polyethylene, polyimide, pellethane, Pebax, Vestamid, Cristamid, Grillamid or any other suitable material known to those of ordinary skill in the art. The two portions are joined together by any number of means known to those of ordinary skill in the art. The stainless steel proximal end gives the shaft the necessary rigidity or stiffness it needs to effectively push out the stent, while the polymeric distal portion provides the necessary flexibility to navigate tortuous vessels.

The distal portion 18 of the shaft has a distal tip 20 attached thereto. The distal tip 20 has a proximal end 34 whose diameter is substantially the same as the outer diameter of the sheath 40. The distal tip tapers to a smaller diameter from its proximal end to its distal end, wherein the distal end 36 of the distal tip has a diameter smaller than the inner diameter of the sheath. Also attached to distal portion 18 of shaft 10 is a stop 22 which is proximal to the distal tip 20. Stop 22 can be made from any number of materials known in the art, including stainless steel, and is even more preferably made from a highly radiopaque material such as platinum, gold tantalum. The diameter of stop 22 is substantially the same as the inner diameter of sheath 40, and would actually make frictional contact with the inner surface of the sheath. Stop 22 helps to push the stent out of the sheath during deployment, and helps the stent from migrating proximally into the sheath 40.

A stent bed 24 is defined as being that portion of the shaft between the distal tip 20 and the stop 22. The stent bed 24 and the stent 50 are coaxial so that the portion of shaft 18 comprising the stent bed 24 is located within the lumen of the stent 50. However, the stent bed 24 does not make any contact with stent 50 itself. Lastly, shaft 10 has a guidewire lumen 28 extending along its length from its proximal end 12 and exiting through its distal tip 20. This allows the shaft 10 to receive a guidewire much in the same way that an ordinary balloon angioplastly catheter receives a guidewire. Such guidewires are well known in art and help guide catheters and other medical devices through the vasculature of the body.

Sheath 40 is preferably a polymeric catheter and has a proximal end 42 terminating at a hub 52. Sheath 40 also has a distal end 44 which terminates at the proximal end 34 of distal tip 20 of the shaft 18, when the stent is in its fully un-deployed position as shown in the figures. The distal end 44 of sheath 40 includes a radiopaque marker band 46 disposed along its outer surface. As will be explained below, the stent is fully deployed when the marker band 46 is lined up with radiopaque stop 22, thus indicating to the physician that it is now safe to remove the apparatus 1 from the body. Sheath 40 preferably comprises an outer polymeric layer and an inner polymeric layer. Positioned between outer and inner layers a braided reinforcing layer. Braided reinforcing layer is preferably made from stainless steel. The use of braided reinforcing layers in other types of medical devices can be found in U.S. Pat. No. 3,585,707 issued to Stevens on Jun. 22, 1971, U.S. Pat. No. 5,045,072 issued to Castillo et al. on Sep. 3, 1991, and U.S. Pat. No. 5,254,107 issued to Soltesz on Oct. 19, 1993, all of which are hereby incorporated herein by reference.

FIGS. 1 and 2 show the stent 50 as being in its fully un-deployed position. This is the position the stent is in when the apparatus 1 is inserted into the vasculature and its distal end is navigated to a target site. Stent 50 is disposed around stent bed 24 and at the distal end 44 of sheath 40. The distal tip 20 of the shaft 10 is distal to the distal end 44 of the sheath 40, and the proximal end 12 of the shaft 10 is proximal to the proximal end 42 of the sheath 40. The stent 50 is in a compressed state and makes frictional contact with the inner surface 48 of the sheath 40.

When being inserted into a patient, sheath 40 and shaft 10 are locked together at their proximal ends by a Touhy Borst valve 8. This prevents any sliding movement between the shaft and sheath which could result in a premature deployment or partial deployment of the stent. When the stent 50 reaches its target site and is ready for deployment, the Touhy Borst valve 8 is opened so that that the sheath 40 and shaft 10 are no longer locked together.

The method under which apparatus 1 deploys stent 50 should be readily apparent. The apparatus 1 is first inserted into a vessel so that the stent bed 24 is at a target diseased site. Once this has occurred the physician would open the Touhy Borst valve 8. The physician would then grasp the proximal end 12 of shaft 10 so as to hold it in place. Thereafter, the physician would grasp the proximal end 42 of sheath 40 and slide it proximal, relative to the shaft 40. Stop 22 prevents the stent 50 from sliding back with the sheath 40, so that as the sheath 40 is moved back, the stent 50 is pushed out of the distal end 44 of the sheath 40. Stent deployment is complete when the radiopaque band 46 on the sheath 40 is proximal to radiopaque stop 22. The apparatus I can now be withdrawn through stent 50 and removed from the patient.

Although particular embodiments of the present invention have been shown and described, modification may be made to the device and/or method without departing from the spirit and scope of the present invention. The terms used in describing the invention are used in their descriptive sense and not as terms of limitations.

That which is claimed is:

1. A stent for insertion into a vessel of a patient, said stent comprising:
   a) a tubular member having a thickness and having front and back open ends and a longitudinal axis extending therebetween, said member having a first smaller diameter for insertion into said vessel, and a second larger diameter for deployment into said vessel; and
   b) said tubular member comprising a plurality of adjacent hoops extending between said front and back ends, said hoops comprising a plurality of longitudinal struts each having opposing ends and a center therebetween, ends of said struts are shaped to form a plurality of loops connecting adjacent struts at said ends of said struts, said member further comprising a plurality of bridges connecting adjacent hoops to one another, said struts having a width measured in an axial direction, said width of said struts being greater at its ends than at its center and wherein said width of said struts at a given point along their center varies in proportion to the cube root of the distance from an end of said strut closest to said given point.

2. The stent according to claim 1 wherein said struts continuously taper from a greater width at its ends to a smaller width at said center.

3. The stent according to claim 1 wherein said stent is a self-expanding stent.

4. The stent according to claim 3 wherein said stent is made from a Nickel Titanium alloy which exhibits superelastic properties at body temperature.

5. The stent according to claim 4 wherein said alloy comprises from about 50.5 percent to about 60 percent Nickel and the remainder comprising Titanium.

6. The stent according to claim 1 wherein said maximum width of said struts are less than said thickness of said tubular member.

7. The stent according to claim 2 wherein said width of said struts at a given point along its center varies in proportion to the cube root of its distance from an end of said strut that said point is closest to.

8. A self-expanding stent for insertion into a vessel of a patient, said stent comprising:
   a) a tubular member made from an elastic material, said tubular material having a thickness and having front and back open ends and a longitudinal axis extending therebetween, said member having a first smaller diameter for insertion into said vessel, and a second larger diameter for deployment into said vessel; and
   b) said tubular member comprising a plurality of adjacent hoops extending between said front and back ends, said hoops comprising a plurality of longitudinal struts each having opposing ends and a center therebetween, said ends of said struts are shaped to form a plurality of loops connecting adjacent struts at said ends of said struts, said member further comprising a plurality of bridges connecting adjacent hoops to one another, said struts having a width measured in an axial direction, said width of said struts continuously taper from a greater width at said ends to a smaller width at said centers.

9. The stent according to claim 8 wherein said stent is made from a Nickel Titanium alloy which exhibits superelastic properties at body temperature.

10. The stent according to claim 9 wherein said alloy comprises from about 50.5 percent to about 60 percent Nickel and the remainder comprising Titanium.

11. The stent according to claim 8 wherein said maximum width of said struts are less than said thickness of said tubular member.

12. The stent according to claim 8 wherein said width of any strut at a given point along its center varies in proportion to the cube root of its distance from an end of said strut that said point is closest to.

13. A stent for insertion into a vessel of a patient, said stent comprising:
   a) a tubular member having a thickness and having front and back open ends and a longitudinal axis extending therebetween, said member having a first smaller diameter for insertion into said vessel, and a second larger diameter for deployment into said vessel; and
   b) said tubular member comprising a plurality of adjacent hoops extending between said front and back ends, said hoops comprising a plurality of longitudinal struts each having opposing ends and a center therebetween, said ends of said struts are shaped to form a plurality of loops connecting adjacent struts at said ends of said struts, said member further comprising a plurality of bridges connecting adjacent hoops to one another, said struts having a width measured in an axial direction, said width of said struts continuously taper from a greater width at said ends to a smaller width at said centers such that a width of any strut at a given point along its center varies in proportion to the cube root of its distance from an end of said strut that said point is closest to.

14. The stent according to claim 13 wherein said stent is made from a Nickel Titanium alloy which exhibits superelastic properties at body temperature.

15. The stent according to claim 14 wherein said alloy comprises from about 50.5 percent to about 60 percent Nickel and the remainder comprising Titanium.

16. The stent according to claim 13 wherein said maximum width of said struts are less than said thickness of said tubular member.

* * * * *